United States Patent [19]

Yamamoto

[11] Patent Number: 4,685,059

[45] Date of Patent: Aug. 4, 1987

[54] METHOD AND APPARATUS FOR MEASURING BODY FLUID CONSTITUENTS AND STORING AND MANAGING THE TEST DATA AND METHOD OF CONTROLLING AND PROCESSING THE TEST DATA

[75] Inventor: Hiroshi Yamamoto, Uji, Japan

[73] Assignee: Kabushiki Kaisha Kyoto Daiichi Kagaku, Japan

[21] Appl. No.: 636,302

[22] Filed: Jul. 31, 1984

[30] Foreign Application Priority Data

Aug. 5, 1983 [JP] Japan .................. 58-144245

[51] Int. Cl.⁴ .................. G06F 15/42; G06G 7/60; G01N 30/96; G01N 21/00
[52] U.S. Cl. .................. 364/415; 422/68; 436/164
[58] Field of Search ............ 364/415, 416; 346/33 A, 346/33 ME; 356/408, 425, 445; 422/56, 68; 436/164; 128/632, 633, 634, 635

[56] References Cited

U.S. PATENT DOCUMENTS

| | | | |
|---|---|---|---|
| 4,373,818 | 2/1983 | Yamamoto et al. | 356/408 |
| 4,509,859 | 4/1985 | Markart et al. | 422/68 X |
| 4,519,398 | 5/1985 | Lisiecki et al. | 346/33 ME X |
| 4,546,436 | 10/1985 | Schneider et al. | 364/415 |

FOREIGN PATENT DOCUMENTS 73437 3/1976 Australia .................. 128/632

Primary Examiner—E. A. Goldberg
Assistant Examiner—Patrick W. Foster
Attorney, Agent, or Firm—Darby & Darby

[57] ABSTRACT

A method for measuring body fluid constituents and storing the test data, which stores the measurement data of body fluid constituents measured by means of a small-size, light-weight, portable analyzing apparatus and a solid reagent, in the memory circuit of the apparatus, and after the required or specified number of measurement data has been stored, delivers the data into an external device. The external action data can also be stored. A method of controlling and processing the test data of body fluid constituents which stores one lot of data groups of each apparatus in an external unit together with the data for identifying the patient and displays the measurements of each patient calculated from one or a plurality of data groups of each analyzing apparatus in digital or analog form.

4 Claims, 5 Drawing Figures

METHOD AND APPARATUS FOR MEASURING BODY FLUID CONSTITUENTS AND STORING AND MANAGING THE TEST DATA AND METHOD OF CONTROLLING AND PROCESSING THE TEST DATA

BACKGROUND OF THE INVENTION

This invention relates to a method and apparatus for recording the measurements which varies with time, together with time measurement data, in various clinical tests and storing the test data at the same time as the measurement to understand the conditions of the patient from the aspect of variation, and method of controlling and processing the test data.

At present, clinical test techniques using various analytical apparatus and reagents for discovery and diagnosis of diseases, ascertaining the medical effect, and monitoring the morbidity change are established and widely applied to many diseases. However, these clinical tests must normally be carried out in medical institutions since they generally require sophisticated techniques and knowledge and the judgment based on the test results require expert knowledge.

On the other hand, ascertaining the medical effect and monitoring the morbidity change require continual measurement. When a long period home treatment is required, regularly going to the hospital is a burden, the patient, physically mentally and economically and neglecting the test can cause problems such as worsening morbidity. The fundamentals of the diabetes remedy, for example, are alimentotherapy, exercise cure, and medical therapy, and, in particular, it is a large problem for a insulin-dependent diabetes patient or a diabetes pregnant woman to control the blood sugar level in a proper range. For this reason the patient has to go to hospital regularly to receive instructions from the doctor while while paying attention to the daily diet.

To solve such inconvenience, a control technique called "home monitoring" or "self monitoring" is being tentatively adopted recently, in which the patient himself performs the various tests using an analytical implement or measuring instrument provided with a simplified measuring reagent (solid reagent) which can be used simply by even a layman. The patient records the measurements on memo paper or the like and reports them later collectively to the doctor for his (and the patient's) inspection of the variation for ascertaining the therapeutical effect, monitoring morbidity change, and for new instructions to the patient. This technique, which can be practiced at home, makes frequent measurement possible and elevates the patient's sense of participation, resulting in a large effect of correct self control in daily life. The solid reagent mentioned here includes a carrier such as paper impregnated with a reagent and film formed of a mixed reagent and polymeric material. The solid reagent is fixed to a strip or piece-shaped backing for convenience to form an analytical implement.

However, in the home monitoring practiced so far, the record by the patient, which is reported to the doctor at the next visit to hospital, is apt to contain errors caused when it is copied for reporting, and copying itself is very troublesome. In addition, a continuous change is difficult to make out unless it is shown graphically, and making a graph requires much trouble. This, together with the copying, limits the number of patients a doctor can deal with. Thus, the home monitoring has many difficulties in practice, though being an excellent technique. Among these difficulties, copying errors and troublesomeness in the patient side and data processing in the doctor side are large problems. Further, accurate recording and copying of the time, quantity, and degree of external action to the patient such as medication and injection, which are important factors, are also troublesome and apt to produce error.

SUMMARY OF THE INVENTION

It is an object of the present invention to promote the home monitoring by increasing the reliability of data and the sense of self-control of the patient by using instrumental analysis.

Another object of the invention is to provide a method for preventing copying error in the patient side and doctor side and saving the burden of labor of patients and labor in the doctor side such as for sorting and graphing the data of many patients, by uniting the measurement and recording. Still another object of the invention is to provide a measurement control means which is small-size and lightweight, and simple, and permits accurate measurement and recording of the data of measurement and measuring time.

DETAILED DESCRIPTION OF THE INVENTION

Figure 1:
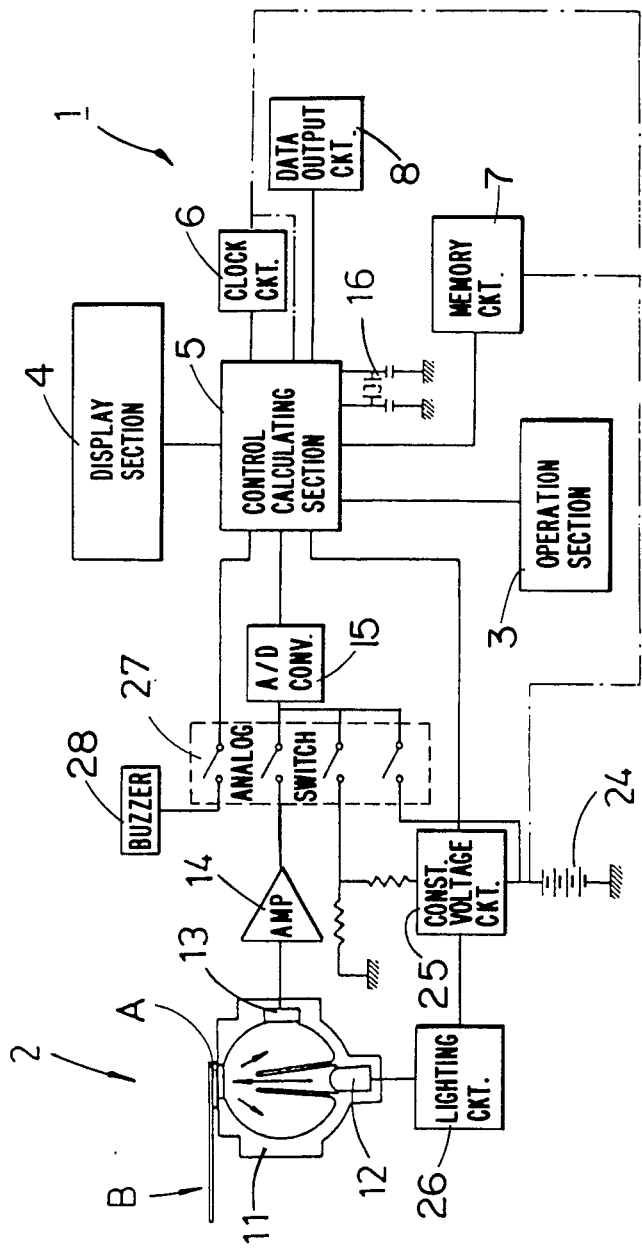
FIG. 1 is a block diagram showing an embodiment of the measurement control means according to the invention.

Referring to the drawings, the method and means of the invention will now be described in detail.

Figure 2:
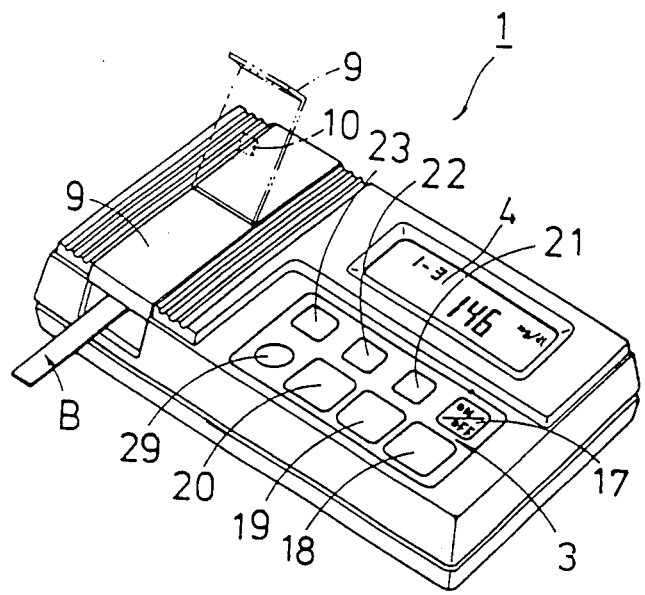
FIG. 2 is a perspective view of the measurement control means shown in FIG. 1.

The measurement control means shown in FIG. 1 and FIG. 2 controls the measurement of the constituents of body fluid and the test data.

This embodiment of the measurement control means (1) is used to measure the glucose concentration in the blood of a diabetes patient and is provided in its analyzing section (2) with an optical system for measuring reflected light. It is mainly composed of an operating section (3), a display section (4), a control calculating section (5), a clock circuit (6), and a data output circuit (8), in addition to the analyzing section (2). In FIG. 2, the symbol (9) indicates an analyzing section cover and (10) indicates a light volume standard reflector. The analyzing section (2) comprises an integrating sphere (11), a light source (12), a light detector (13), an amplifier (14), and and A-D convertor (15). The control calculating section (5) comprises a one-chip microcomputer containing an oscillating circuit, a CPU, ROM, RAM, and I/O. Operation section (3) is provided with an ON/OFF key (17), start key (18), measure key (19), calibration key (20), memory store key (21), memory read key (22), and a memory clear key (23). In FIG. 1, the symbol (24) indicates a dry cell as the driving source, (25) is a constant voltage circuit, (26) is a lighting circuit, (27) is an analogue switch, and (28) is a buzzer. The use of a dry cell (including charging type) makes the whole apparatus small-size and light-weight and portable. However, it is possible, of course, to use an AC adaptor or a commercial power supply directly.

The procedure of blood sugar concentration measurement using the means (1) shown in FIG. 1 will now be described. Before the measurement, prepare an analyzing implement (B) provided with the solid reagent (A) for glucose analysis and the blood sample, and turn on the power supply by pressing the ON/OFF key (17). Then, press the start key (18) to actuate the oscillating circuit (16) and use it as the timer. The oscillating circuit (16) which is actuated by the operation of the ON/OFF key (17) not only tells 60-sec and 120-sec time elapses but also serves as the timing standard for the actions of the control calculating section (5). At the same time as pressing the start key, apply the sample to the solid reagent (A) of the analyzing implement (b). After 60 sec when the buzzer (28) sounds, wipe off surplus blood, set the analyzing implement (B) to the analyzing section (2), and close the cover (9). After 10 sec, the buzzer (28) sounds again and the light source lights at the same time. The light reflected on the surface of the reacted solid reagent is converted into an electric signal and, in turn, into a digital signal by the A-D convertor (15), and inputted into the control calculating section (5).

The reflectance on the surface of the solid reagent (A) is determined as the relative reflectance to the light volume (standard amount of signal) from the light volume standard reflector (10) measured when the power source is switched on, or the start key (18) is pressed. The blood sugar concentrations calculated from this relative reflectance and the calibration curve which is set in the control calculating section (5) and is displayed on the display section (4). The calibration curve is set by the following procedures:

Press the calibration key (20) after turning on the power supply to bring the mode into calibration mode. Set standard reflection pieces (or solid reagents applied with the standard solution) for low concentration and high concentration in the analyzing section and press the measure key (19). By this operation, the calibration values are stored in the memory of the control calculation section (5), and retained even after the power supply switch is turned OFF. Therefore, it need not be set every time, but be set as required only when the dry cell is replaced, when the lot of the analyzing implement is changed, or when the ambient temperature has been largely changed.

If the memory-store key (21) is pressed when the measurements are displayed on the display section (4), the measured values are stored in the memory circuit (7). At the same time, the output data from the clock circuit, that is, date and measuring time, are automatically read and stored additionally. Further, the counting circuit gives serial numbers to the data of the same date. The date can be calendar day (year, month, day) with hour and minute or an elapsed day in a series of measurements with time roughly in 2-hour unit to save the capacity of the memory circuit (7). The measured data can be stored automatically at the same time as displayed on the display section (4). Further, a memory backup cell can be provided to prevent the advertent erosure of the measurements and the calibration data from the memory when the cell (24) is replaced.

Measured data stored in the memory circuit (7) through mistake can be cleared, if immediately after, by pressing the memory clear key (23). Measured data stored before it if no, can all be cleared by pressing the memory read key (22) and memory clear key (23) simultaneously, and the elapsed-days timer is reset at the same time.

The memory read key (22) is also used to read the stored measured data, and permits one-by-one display of the stored data, as required, on the display section (4). When this key (2) is held pressed, the stored data are called out successively on the display section (4).

The action key (29) is operated when some external actions such as insulin injection, medication, and sugar administration for sugar load test are taken, to display the fact and the time of the action on the display section (4) and to store them in the memory circuit (7). This key is provided as required. Further, a ten key (not shown) can be provided on the measurement control means (1) to record one dose of insulin or other medicine administration. In these cases also, it can be stored in the memory circuit (7) by pressing the memory-store key (21) when it is displayed on the display section, like in the case of measured data, or can be automatically stored in the memory circuit simultaneously with the display on the display section (4). The data stored by mistake can be cleared by means of the memory clear key (23).

Thus, measured data and external action records (and quantity of medicine) are stored in the memory circuit (7) together with the data generated by the clock circuit (6) at each time to give the understanding of the influence of external action on the measurements simply and certainly. Since the external action such as injection and medication is provided under the instruction of a doctor, the time of external action and for example, the dose of insulin may be inputted into the external unit by the doctor.

In such manner, the patient operates the measurement control means (1) by himself and stores many data of the blood sugar at regular times every day or successive blood sugar level change in a specified day into the memory circuit (7) can obtain rough sense of the blood sugar level variation, physical conditions, and therapeutical effects by calling out all the stored measurement data or data measured in a specified day.

Figure 3:
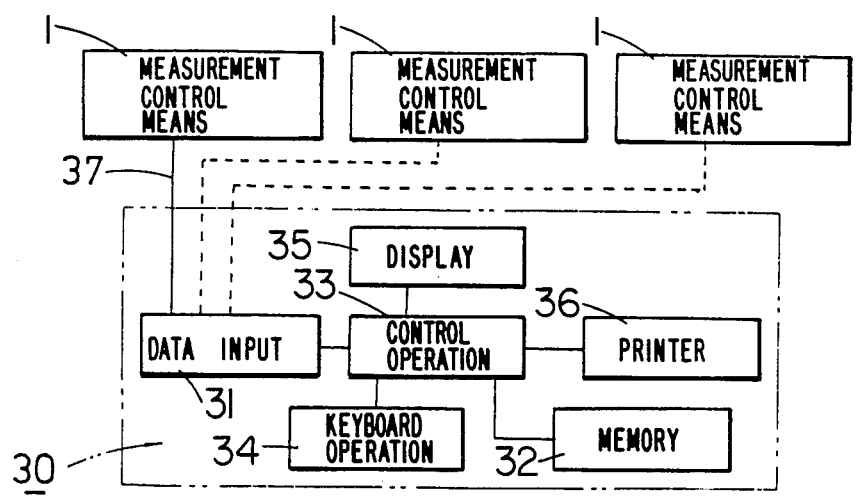
FIG. 3 is a block diagram showing an embodiment of the data storing means according to the invention.

The patient goes to the hospital or diabetes center about twice a month (or whenever the condition of disease is getting worse or changes suddenly) and hands over the measurement control means (1) to the doctor. The doctor connects the data output circuit (8) of the submitted measurement control means (1) to the data input circuit (31) of a data collecting unit (30), an external means shown in FIG. 3, and press the memory read key (2) of the measurement control means (1) to transfer the data stored in the memory circuit (7) of the measurement control means (1) to the memory circuit (3) of the data collecting unit. The memory read key (22) also serves to check the connection of the connector of the data output circuit (8). In FIG. 3, the symbol (33) indicates the control operation section, the symbol (35), the display section, and (36), the printer section of the data collecting unit (30), The measurement control means (1) can be connected to the data collecting unit (30) through a connector (37) or by means of an indirect method such as the use of a telephone circuit and acoustic coupler.

In the above embodiment, the output of the measurement control means (1) is directly transferred from the data output circuit (8) to the data input circuit of the data collecting unit (30). It is also possible, however, that the measured data are successively displayed on the display section (4) of the measurement control means (1), and the doctor, nurse, or inspector keys the data into the data collecting unit (30) while watching the display. In this case, the data output circuit (8) of the measurement control means (1) can be omitted.

When a total set of data stored in the measurement control means (1) has been transferred into the memory circuit (32) of the data collecting unit (30), the buzzer (28) of the measurement control means (1) notifies it. At the same time, the total data which have been stored are automatically [or by key operation or by the instruction from the data collecting unit (30)] erased, and the elapsed-days timer is reset for the next operation.

The data collecting unit (30), on the other hand, displays the total set of data on the CRT of the display section (35) according to the operation of the key in the keyboard operation section (34), in the a form of table (shown in FIG. 4) a or graph (shown in FIG. 5), as required. The doctor keys in the information such as name, age, sex distinction, and code number required for identifying the patient on the group of data, and supplementary data such as date, time, and quantity of insulin injection. These information can be keyed in prior to the transfer of the total data in each time of each measurement control means (1) including the case where data of many measurement control means (1) are successively transferred. The input of the supplementary data is unnecessary when the patient directly keys the data into the measurement control means.

Figures 4, 5:
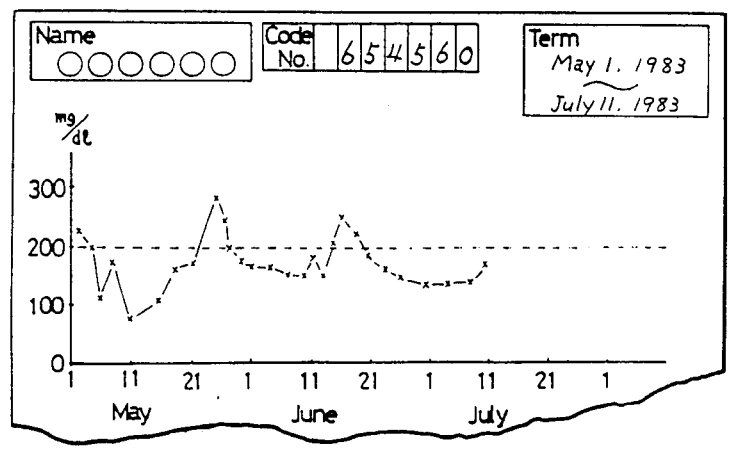
FIGS. 4 and 5 show a Table and Graph printed out by the data storing means.

Data, tables, and graphs displayed on the CDT can be printed in the printer section (36). This permits the grasp of the aspect of the blood sugar level control at a glance. On the table, the name, age, and sex distinction of the patient, serial number in the order of measuring time, date of measurement, time, measured value, and serial number in one measured date are printed (FIG. 4). In the column of comment in FIG. 4, the prescription of the doctor, quantity of insulin injection and its date and time, etc. are entered. In the case of graph (FIG. 5), the quantity, date, and time of insulin injection can be shown, for example, by the length and position of a line on the upper side of the broken-line graph. It is also possible in preparing a table or graph to instruct the control limit; in a table, affix an upward or downward arrow to the data as a comment, or in a graph, draw limit lines.

When all the data in a set are read or printed out from the measurement control means (1) as required, it is possible to give a group name to a set of data and store the data group in another memory means (e.g. floppy disk) and call it out when required for use. The data in the floppy disk, for example, can be retrieved by a retrieval program and used for seeing the progress of all the past measurements of the same patient or for examining similar cases. The floppy disk provides various edition such as linkage of data row, insertion, and deletion, in addition to the data storage.

The method according to the invention is not limited in application to the determination of the blood sugar level as described so far in connection with the means shown, but can be applied to the determination of other items of body fluid. In addition, the analyzing section (2) of the measurement control means (1) can have a structure for measuring the amount of fluorescence instead of that of reflected light for a measuring item adapted to the fluorometry. On the other hand, the external device can be only a printer or a recording and printing device without editing function, other than the data collecting unit (personal computer, minicomputer, or macro computer) provided with a control calculating section and memory circuit. The measurement control means (1) can be used individually by in-patients in a hospital or used for the body fluid constituent measurement and the storage of test data of plural number of patients in a private hospital, in addition to the use a home monitoring in general homes. When using it for plural number of patients pressing the measure key (19) to immediately start using the immediate measuring function is preferable to pressing the start key (18) to start the timer for normal automatic operation, since this takes more time.

As detailed above, the method according to the invention stores in the memory circuit of the analyzing apparatus the measurement data of body fluid constituents obtained by use of a small-size, light-weight, portable analyzing apparatus provided with a reflectometer or fluorophotometer and a solid reagent, and the data produced by a clock circuit showing the time the measurement was performed, and when an as-required or specified number of measurement data have been accumulated, it stores the data in an external device. Further, it stores in the external device a lot of data group from individual apparatus together with the information for identifying the patient, and from one or more lots of data group obtained from a single analyzing apparatus, displays the variation of measurement with time of a patient in digital or analogue form. According to the method of the invention, no recording of the measurement data and measuring time is required, accurate data are obtained, data copying error is prevented and the labor burden is decreased in the patient side, and data copying error is prevented and labor such as copying, sorting, and graphing of many patients data is saved in the doctor side. In addition, data readily arranged into tables and graphs make the condition of disease and therapeutical effect clear and evident, leading to very easy home monitoring system. The method of the invention further has many advantages such that the therapeutical effect is raised by urging the self-consiousness of the patient by giving him a target, for example, of the blood sugar level control, the change of the disease condition can be estimated from the past data, or that the clue for remedy is obtained from the same trend of data of himself and other patient.

The measurement control means according to the invention provides determination of body fluid constituents and the storage of test data and data of measuring time by the same unit and is small-size, light-weight, and portable, permitting the use in anywhere. It provides reliable measurement by very simple and secure operation. Therefore, each of athome patients and in-patients can make self-control by use of it and the doctor can easily control many patients using one data collecting unit.

I claim:

1. A small-size, light-weight apparatus for measuring body fluid constituents and storing and managing the test data, comprising an analyzing section which optically measures a body fluid sample by use of a solid reagent, a microcomputer which receives the electric signal generated in the analyzing section, determines the timing of measurement, calculates the measured value from the amount of said received electric signal with reference to the standard amount of signal and calibration curve stored in the microcomputer, an operating section which gives operation instruction to the microcomputer from the outside, a display section which displays the results of measurement together with the instruction of operating procedure and operation redoing, a clock circuit, and a memory circuit which stores the results of measurement and the output of the clock circuit when the measurement is performed.

2. An apparatus for measuring body fluid constituents and storing and managing the test data as claimed in claim 1, which apparatus is provided with a data output circuit for delivering the data stored in the memory circuit to the external device for data processing.

3. An apparatus for measuring body fluid constituents and storing and managing the test data as claimed in claim 1 or claim 2, wherein said operating section is provided with a memory store key for storing the results of measurement displayed on the display section into the memory circuit, a memory clear key for erasing measurement data, and a memory read key for calling out the measurement data on the display section.

4. An apparatus for measuring body fluid constituents and storing and managing the test data as claimed in claim 3, wherein an action key and a ten key are provided which are used when an external action is applied to the human body.

* * * * *